(12) United States Patent
Wang (10) Patent No.: US 10,182,864 B2
(45) Date of Patent: *Jan. 22, 2019

(54) IRRIGATED ABLATION CATHETER HAVING A FLEXIBLE MANIFOLD

(71) Applicant: St. Jude Medical, Atrial Fibrillation Division, Inc., Saint Paul, MN (US)

(72) Inventor: Huisun Wang, Maple Grove, MN (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 194 days.

This patent is subject to a terminal disclaimer.

(21) Appl. No.: 14/610,843

(22) Filed: Jan. 30, 2015

(65) Prior Publication Data

US 2015/0202000 A1    Jul. 23, 2015

Related U.S. Application Data

(63) Continuation of application No. 12/326,579, filed on Dec. 2, 2008, now Pat. No. 8,974,453.

(51) Int. Cl.
*A61B 18/00* (2006.01)
*A61B 18/14* (2006.01)

(52) U.S. Cl.
CPC ........ *A61B 18/1492* (2013.01); *A61B 2018/00029* (2013.01); *A61B 2018/00577* (2013.01); *A61B 2218/002* (2013.01)

(58) Field of Classification Search
CPC ...... A61B 18/1492; A61B 2018/00577; A61B 2018/00029; A61B 2218/002
See application file for complete search history.

(56) References Cited

U.S. PATENT DOCUMENTS

| 5,056,517 A | 10/1991 | Fenici |
| 5,230,349 A | 7/1993 | Langberg |

(Continued)

FOREIGN PATENT DOCUMENTS

| WO | 2005048858 A1 | 6/2005 |
| WO | 2005112814 A2 | 12/2005 |

(Continued)

OTHER PUBLICATIONS

Author: Wittkampf, Fred H. Title: Saline-Irrigated Radiofrequency ablation electrode with external cooling Citation: Journal of Cardiovascular Electrophysiology, vol. 16, No. 3 Publication Date: Mar. 2005.

(Continued)

*Primary Examiner* — Jenna Zhang
(74) *Attorney, Agent, or Firm* — Dykema Gossett PLLC (57) ABSTRACT

An irrigated ablation catheter includes a shaft having a proximal end, a distal end, and an irrigation lumen therein. The catheter further includes an electrode assembly coupled to the distal end of the shaft. The electrode assembly includes an ablation electrode and a manifold. The manifold is coupled to each of the distal end of the shaft and the proximal end of the electrode. At least a portion of the manifold is constructed of a flexible material to allow the electrode assembly to deflect. The manifold includes a body, an inner cavity within the body configured for fluid communication with the irrigation lumen, and an irrigation port also within the body and configured for fluid communication with the inner cavity. The irrigation port extends from the inner cavity to the outer surface of the body, and is configured to allow for an irrigating fluid to be distributed from the manifold.

16 Claims, 9 Drawing Sheets

(56) References Cited

U.S. PATENT DOCUMENTS

| | | | |
|---|---|---|---|
| 5,348,554 A | 9/1994 | Imran et al. | |
| 5,403,311 A | 4/1995 | Abele et al. | |
| 5,423,811 A | 6/1995 | Imran et al. | |
| 5,431,168 A | 7/1995 | Webster, Jr. | |
| 5,462,521 A | 10/1995 | Brucker et al. | |
| 5,545,161 A | 8/1996 | Imran | |
| 5,643,197 A | 7/1997 | Brucker et al. | |
| 5,676,693 A | 10/1997 | LaFontaine | |
| 5,769,618 A | 6/1998 | Ono | |
| 5,792,140 A | 8/1998 | Tu et al. | |
| 5,814,029 A | 9/1998 | Hassett | |
| 5,843,152 A | 12/1998 | Tu et al. | |
| 5,913,856 A | 6/1999 | Chia et al. | |
| 5,919,188 A | 7/1999 | Shearon et al. | |
| 5,971,968 A * | 10/1999 | Tu | A61M 25/007 604/103.01 |
| 6,017,338 A | 1/2000 | Brucker et al. | |
| 6,120,476 A * | 9/2000 | Fung | A61B 18/1492 604/528 |
| 6,162,219 A | 12/2000 | Nilsson et al. | |
| 6,168,594 B1 | 1/2001 | LaFontaine et al. | |
| 6,171,275 B1 | 1/2001 | Webster, Jr. | |
| 6,217,576 B1 | 4/2001 | Tu et al. | |
| 6,238,393 B1 | 5/2001 | Mulier et al. | |
| 6,363,937 B1 | 4/2002 | Hovda et al. | |
| 6,602,242 B1 | 8/2003 | Fung et al. | |
| 6,611,699 B2 | 8/2003 | Messing | |
| 7,166,105 B2 | 1/2007 | Mulier et al. | |
| 8,256,428 B2 * | 9/2012 | Hindricks | A61B 18/1492 128/898 |
| 2002/0007181 A1 | 1/2002 | Zikorus | |
| 2002/0058866 A1 * | 5/2002 | Segner | A61M 25/01 600/374 |
| 2002/0087156 A1 | 7/2002 | Maguire et al. | |
| 2003/0212394 A1 | 11/2003 | Pearson et al. | |
| 2004/0054272 A1 | 3/2004 | Messing | |
| 2004/0243121 A1 * | 12/2004 | Lee | A61B 5/0422 606/41 |
| 2005/0177151 A1 | 8/2005 | Coen et al. | |
| 2006/0074414 A1 * | 4/2006 | Mulier | A61B 18/1402 606/45 |
| 2006/0184165 A1 | 8/2006 | Webster, Jr. et al. | |
| 2007/0156131 A1 * | 7/2007 | Datta | A61B 18/1492 606/41 |
| 2007/0270791 A1 * | 11/2007 | Wang | A61B 18/148 606/41 |
| 2008/0045943 A1 * | 2/2008 | Wittkampf | A61B 18/1492 606/41 |
| 2008/0071267 A1 * | 3/2008 | Wang | A61B 18/1492 606/41 |
| 2009/0163911 A1 * | 6/2009 | Cao | A61B 18/1492 606/41 |
| 2009/0163913 A1 * | 6/2009 | Wang | A61B 18/1492 606/41 |

FOREIGN PATENT DOCUMENTS

| | | |
|---|---|---|
| WO | 2007136979 A2 | 11/2007 |
| WO | 2008045925 A2 | 4/2008 |

OTHER PUBLICATIONS

Author: Wittkampf, Fred H. Title: Radiofrequency ablation with a cooled porous electrode catheter Citation: JACC vol. II, No. 2; 17a Publication Date: Feb. 1988.

* cited by examiner

IRRIGATED ABLATION CATHETER HAVING A FLEXIBLE MANIFOLD

CROSS-REFERENCE TO RELATED APPLICATIONS

This application is a continuation of U.S. application Ser. No. 12/326,579, filed 2 Dec. 2008 (the '579 application), now U.S. Pat. No. 8,974,453, issued on 10 Mar. 2015. The '579 application is each hereby incorporated by reference as though fully set forth herein.

BACKGROUND OF THE INVENTION a. Field of the Invention

The present invention relates to electrophysiological (EP) catheters. More particularly, the present invention relates to an irrigated EP catheter for use in ablation procedures, that includes a flexible manifold disposed between the shaft and electrode assembly of the catheter.

b. Background Art

It is known to use catheters to perform a variety of functions relating to diagnostic and therapeutic medical procedures. Electrophysiological (EP) catheters find particular application in cardiac electrophysiology studies and procedures, such as various cardiac diagnostic and/or ablation procedures. In ablation procedures, electrodes mounted or otherwise disposed at the distal end of the catheter may be used to deliver energy to the heart to ablate a site of cardiac tissue that causes, for example, an arrhythmia or abnormality in the heart rhythm.

Because ablation procedures may generate significant heat, which if not controlled can result in excessive tissue damage, such as, for example, steam pop, tissue charring, and the like, it is desirable to include a mechanism to irrigate the target area and the ablating electrode(s) with biocompatible fluids, such as, for example, saline solution. The use of irrigated catheters can also prevent the formation of soft thrombus and/or blood coagulation during ablation procedures.

Typically, there are three classes of irrigated catheters used in ablation procedures—open, closed, and external irrigated catheters. Closed irrigated catheters usually circulate a cooling fluid within the inner cavity or lumen disposed proximate the ablation electrode.

Open irrigated catheters typically deliver the cooling or irrigating fluid through irrigation ports or outlets to a surface of the ablation electrode. Open irrigated catheters use an inner cavity or lumen of the electrode to distribute saline solution, or other irrigating fluids known in the art, to one or more irrigation ports or outlets disposed within the electrode and between the inner cavity and outer surface of the electrode. Thus, the irrigating fluid flows through the irrigation ports onto the surface of the electrode. However, one drawback of this particular type of irrigated catheter is that the flow of the irrigating fluid through the electrode lowers the temperature of the electrode during operation, often making accurate monitoring and control of the ablative process more difficult.

External irrigated catheters provide one solution to this drawback. More particularly, rather than distributing irrigating fluid directly from the electrode of the catheter, as is done in open irrigated catheters, external irrigated catheters use a fluid manifold disposed between the catheter shaft and the electrode to distribute irrigation fluid from the catheter. More particularly, the manifold distributes irrigation fluid to the external surface of the electrode to cool the electrode and to also minimize the blood coagulation. Accordingly, it is known that external irrigated ablation catheters typically include, in part, a shaft having a proximal end and a distal end, and an electrode assembly disposed at the distal end of the shaft that is comprised of a proximal manifold portion and a distal electrode portion. Therefore, the manifold is disposed between and coupled to each of the distal end of the shaft and the proximal end of the electrode. In known systems, the manifold typically includes an inner cavity configured for fluid communication with an irrigation lumen in the shaft of the catheter. The manifold further includes a plurality of irrigation ports configured for fluid communication with the inner cavity to distribute irrigating fluid passing from the irrigation lumen, to the inner cavity, and then on to the surface of the ablation electrode and/or surrounding tissue.

These known arrangements, however, are not without their drawbacks. For instance, in ablation procedures, it is often desirable to create a deep lesion on the cardiac tissue. In order to do so, it is important to have adequate contact between the electrode of the catheter and the cardiac tissue being ablated. However, the manifold of typical external irrigated ablation catheters is usually formed of rigid plastic materials, such as, for example, polyetheretherketone (PEEK), having little to no flexibility. As such, optimal contact between the electrode and the cardiac tissue may not be achieved because the electrode assembly cannot be sufficiently deflected due to the rigidity of the manifold.

Another drawback lies in the distribution of the irrigating fluid from the manifold. In known arrangements, irrigating fluid is equally distributed from all of the irrigation ports disposed in the manifold regardless of the relative location of the irrigation port in relation to the site where the ablation function or operation is performed. Accordingly, fluid is distributed or expelled from the manifold to areas where irrigation is not needed, and thus, irrigating fluid is unnecessarily wasted.

Accordingly, there is a need for a catheter that will minimize and/or eliminate one or more of the above-identified deficiencies.

BRIEF SUMMARY OF THE INVENTION

The present invention is directed to an irrigated ablation catheter, the constituent components, and a method of manufacturing the same. The catheter according to the present teachings includes a shaft having a proximal end and a distal end, and an irrigation lumen disposed therein. The catheter further includes an electrode assembly having a distal portion defined by an ablation electrode and a proximal portion defined by a manifold. The manifold is disposed between and coupled to each of the shaft and the electrode components of the catheter. The manifold is constructed of a flexible material that allows for the electrode assembly of the catheter, and therefore, the manifold and the electrode, to deflect.

In accordance with one aspect of the invention, the manifold includes a body defined by an outer surface, an inner cavity disposed within the body configured for fluid communication with the irrigation lumen, and an irrigation port disposed within the body and configured for fluid communication with the inner cavity. The irrigation port is a through-going port extending from the inner cavity to the outer surface of the body and is configured to allow for an irrigating fluid to be distributed from the manifold.

In an exemplary embodiment, the manifold, and the body thereof, in particular, includes a first portion, a second portion, and a third portion. The first portion is disposed at a first end of the body and is configured to be coupled to the shaft of the catheter. The second portion is disposed at a second end of the body opposite the first end, and is configured to be coupled to the electrode of the catheter. The third portion is disposed between the first and second portions. At least one of the first, second, and third portions are constructed of a flexible material. As described above, the manifold further includes an inner cavity and an irrigation port that are disposed within the body, with the inner cavity extending through at least the first and third portions of the body.

The method of manufacturing an irrigated ablation catheter comprising a shaft and an ablating electrode in accordance with the present teachings includes providing a manifold having an inner cavity and an irrigating port disposed therein, wherein at least a portion of the manifold is constructed of a flexible material. The method further includes coupling the manifold to the distal end of the shaft. The method still further includes coupling the manifold to the electrode.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
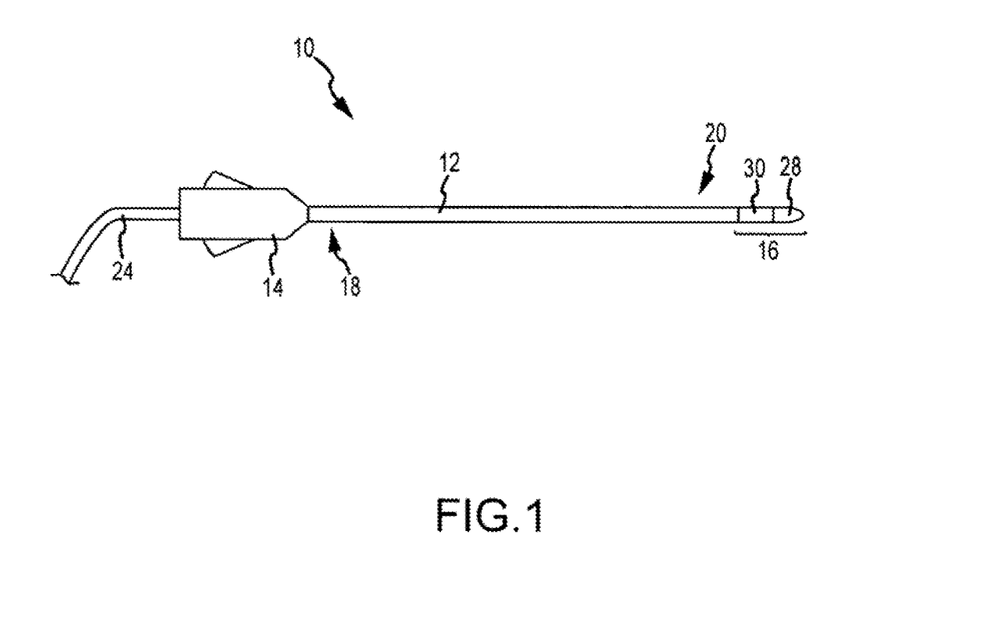
FIG. 1 is a diagrammatic view of an irrigated ablation catheter in accordance with the present teachings.
Figure 2:
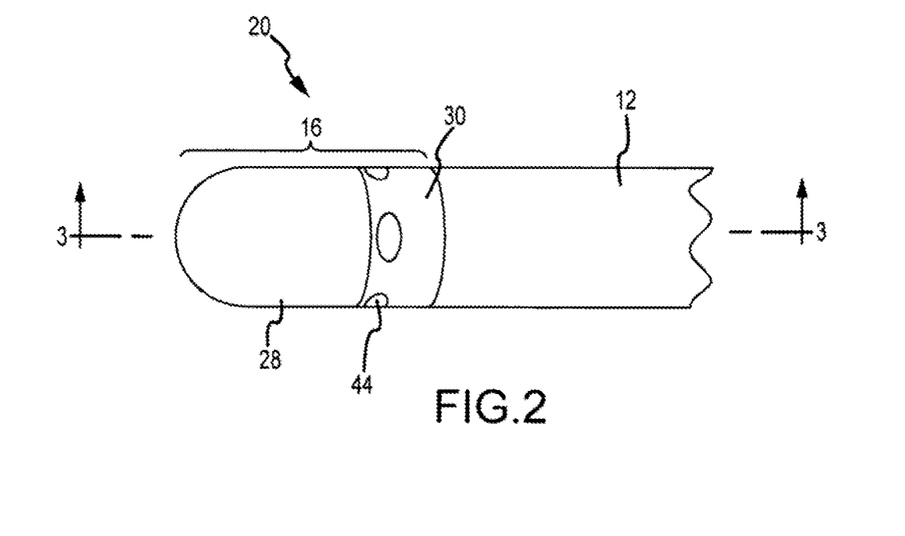
FIG. 2 is a plan view of the distal portion of the irrigated ablation catheter illustrated in FIG. 1.

Referring now to the drawings wherein like reference numerals are used to identify identical components in the various views, FIGS. 1 and 2 illustrate one exemplary embodiment of an irrigated electrophysiological (EP) catheter 10. In its most general form, the catheter 10 includes an elongated shaft 12, a handle 14, and an electrode assembly 16. The catheter 10 may be used in a number of diagnostic and therapeutic applications, such as the recording of electrograms in the heart, the performance of a cardiac ablation procedure, and other similar applications/procedures. Accordingly, one of ordinary skill in the art will recognize and appreciate that the inventive catheter can be used in any number of diagnostic and therapeutic applications.

Figure 3:
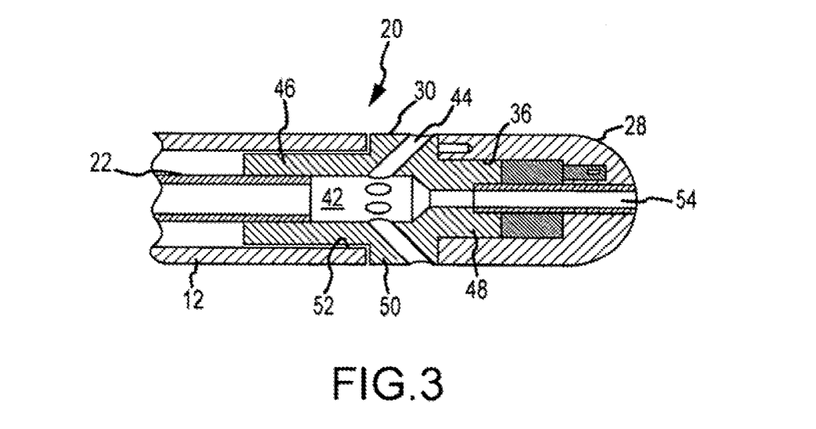
FIG. 3 is a cross-sectional view of the distal portion of the irrigated ablation catheter illustrated in FIGS. 1 and 2 taken substantially along the lines 3-3 in FIG. 2.

With reference to FIGS. 2 and 3, the shaft 12 extends along an axis and includes a proximal end 18 and a distal end 20. The shaft 12 may be formed of one or more materials known in the art. These materials include, without limitation, PEBAX, Nylon, and polyurethane. In an exemplary embodiment, the shaft 12 may be constructed, at least in part, of a metal wire braid, as is known in the art. The shaft 12 further includes at least one, and typically multiple, lumens therein (best shown in FIG. 3). The lumens extend longitudinally along an axial portion of the shaft 12 from the proximal end 18 to the distal end 20, and are configured to have one or more catheter components disposed therein, such as, for example, pull wires, planarity wires, and/or lead wires for electrodes associated with the catheter 10. At least one lumen, lumen 22, is an irrigation lumen (or irrigation tube disposed within the shaft 12) in which irrigating fluid flows. The irrigation lumen 22 is coupled to, and/or in fluid communication with, an irrigating fluid source that provides biocompatible irrigating fluid, such as, for example, saline or other irrigating fluids known in the art, to the catheter 10. Accordingly, as illustrated in FIG. 1, the catheter 10 may further include a connecting tube 24 to couple the fluid source (not shown) with the lumen 22.

With continued reference to FIG. 1, the handle 14 is coupled to the shaft 12 at the proximal end 18 thereof. The handle 14 is operative to, among other things, to effect movement of the shaft 12, or steer the catheter 10, when the catheter 10 is disposed within a patient. The handle 14 includes an actuator 26 that can be selectively manipulated to navigate the catheter 10 and to position the distal end 20 thereof in a desired location.

As illustrated in FIGS. 2 and 3, the electrode assembly 16 is coupled to the shaft 12 at the distal end 20 thereof. More particularly, as will be described in greater detail below, the electrode assembly 16 comprises a distal portion defined by an electrode 28, and a proximal portion defined by a manifold 30. In an exemplary embodiment, the shaft 12 is coupled to a first or proximal end 32 of the manifold 30, and the electrode 28 is coupled to a second or distal end 34 of the manifold 30. The electrode 28, which may be constructed of one or more materials known in the art, is an ablation electrode operative to deliver energy to the heart to ablate a site of cardiac tissue. In one exemplary embodiment, the electrode 28 further includes a recessed cavity or pocket 36 that, as will be described in greater detail below, is configured to receive a portion of the manifold 30, such that the manifold 30 and the electrode 28 may be coupled together.

As briefly described above, and as illustrated in FIGS. 2 and 3, for example, the manifold 30 is disposed between, and coupled to, each of the distal end 20 of the shaft 12 and the electrode 28. The manifold 30 will be described in greater detail with reference to FIGS. 4 and 5.

Figure 4:
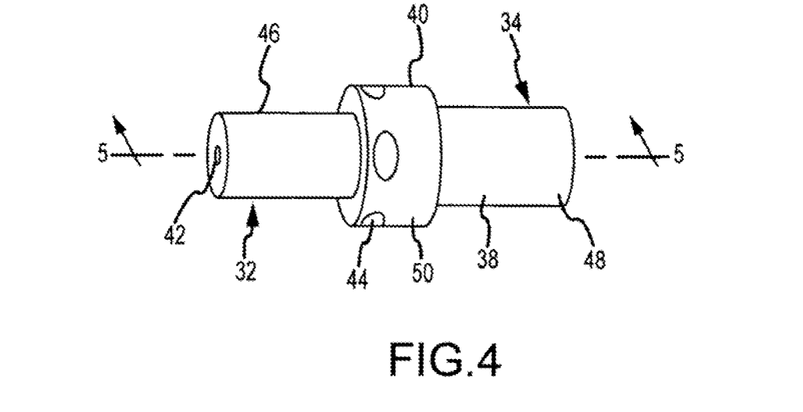
FIG. 4 is an enlarged view of the manifold of the irrigated ablation catheter illustrated in FIGS. 1-3.
Figure 5:
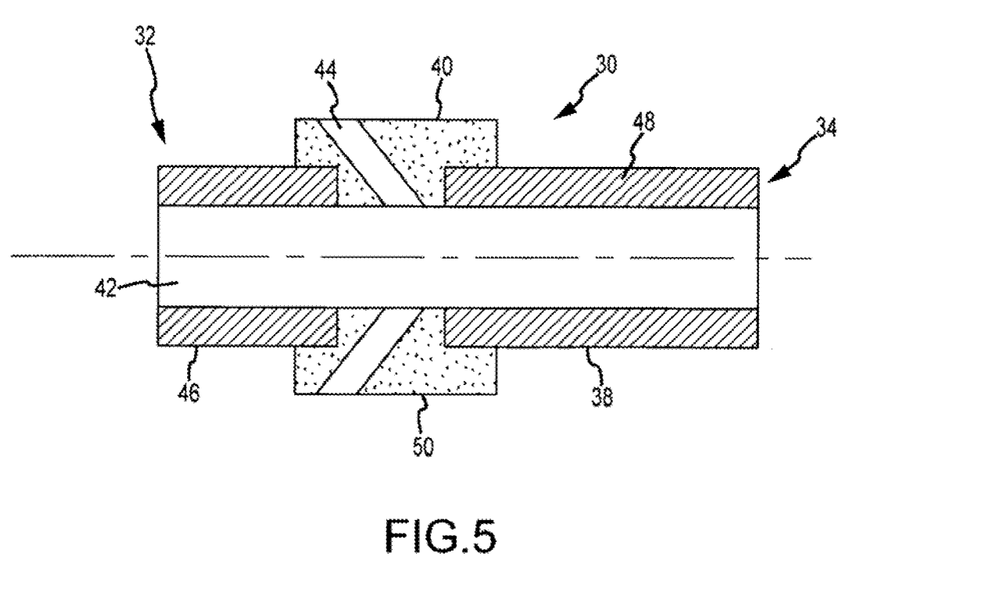
FIG. 5 is a cross-sectional view of the manifold illustrated in FIGS. 1-4 taken substantially along the lines 5-5 in FIG. 4.

In its most general form, the manifold 30 comprises a body 38 defined by an outer surface 40. As briefly described above, the body 38 has a first or proximal end 32 configured to be coupled with the distal end 20 of the shaft 12, and a second or distal end 34 configured to be coupled with the electrode 28. Unlike known ablation catheter assemblies wherein the manifold is formed of a rigid plastic, such as, for example, PEEK, at least a portion of the manifold 30 is constructed of a at least one flexible material. Constructing the manifold 30 of a flexible material allows for the electrode assembly 16, and therefore, the manifold 30 and the electrode 28, to be deflected when the electrode 28 contacts tissue and a sufficient amount of deflection force is applied to the electrode 28 against the tissue by the operator of the catheter 10. In an exemplary embodiment, the flexible material is both flexible and elastic, such as, for exemplary purposes only, an elastic polymer having a durometer that allows the manifold 30 to elastically deform or bend/deflect. In an exemplary embodiment, the durometer of the material is approximately 20-30 D. Additionally, the material must be electrically nonconductive and have poor thermal conduction properties. Suitable materials include, without limitation, silicone, polyurethane, Nylon, PEBAX, and other like materials having similar properties.

With continued reference to FIGS. 4 and 5, the manifold 30 further includes an inner cavity 42 disposed in body 38 that, when the manifold 30 is assembled with the shaft 12, is configured for fluid communication with the irrigation lumen 22. The manifold 30 still further includes at least one, and typically a plurality, of irrigation ports 44 disposed in body 38. In the embodiment illustrated in FIG. 5, the inner cavity 42 comprises a through-going bore extending from the first end 32 of the body 38 to the second end 34 of the body 38. However, in another exemplary embodiment, the inner cavity 42 is not a through-going bore, but rather extends from the first end of the body 38 to a point short of the second end 34 of the body 38. Accordingly, the present invention is not meant to be limited to an embodiment wherein the inner cavity 42 comprises a through-going bore.

Figure 6A:
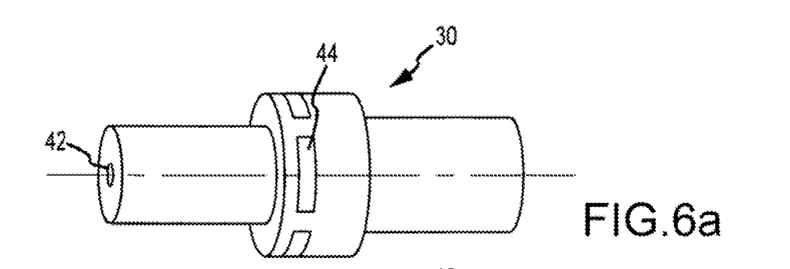
FIGS. 6a-6d are enlarged views of alternate exemplary embodiments of the manifold illustrated in FIGS. 1-5 having differently shaped irrigation ports therein.
Figure 6B:
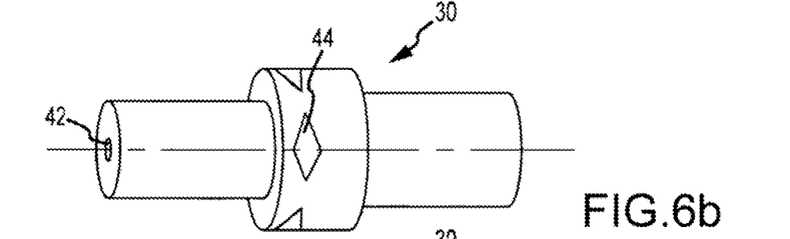
Figure 6C:
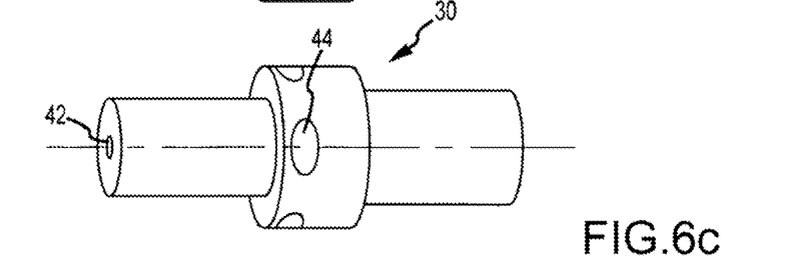
Figure 6D:
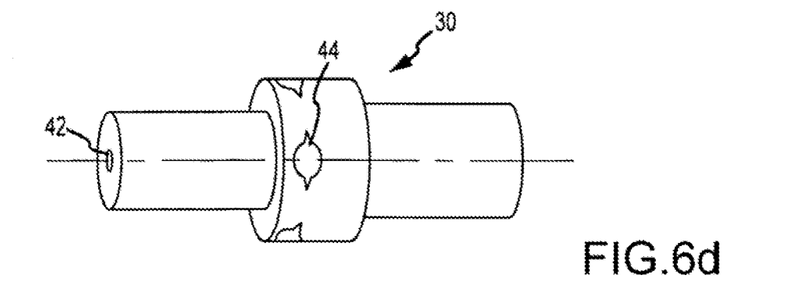

With continued reference to FIG. 5, the irrigation ports 44 are configured for fluid communication with the inner cavity 42 and extend from the inner cavity 42 to the outer surface 40 of the body 38. The irrigation ports 44 allow for irrigating fluid to be distributed from the manifold 30. More particularly, irrigating fluid flowing in the irrigation lumen 22 flows through the inner cavity 42, and then through the irrigation ports 44 where the fluid is then distributed to the outer surface of electrode 28 and the tissue proximate the irrigation ports 44. In the embodiment illustrated in FIG. 4, the irrigation ports 44 have an oval shape. However, the present invention is not limited to irrigation ports having such a shape. Rather, the irrigation ports 44 may have any number of shapes. For example, in the exemplary embodiments illustrated in FIGS. 6a-6d, the irrigation ports 44 may have a rectangular shape (FIG. 6a), a diamond shape (FIG. 6b), an oval shape (FIG. 6c), and a round or circular shape with a v-shaped cut therein (FIG. 6d). Accordingly, the present invention is not limited to one particular shape for irrigation ports 44.

In the embodiment illustrated in FIGS. 4 and 5, the manifold 30, and more specifically the body 38 thereof, includes a first portion 46 disposed at the first end 32, a second portion 48 disposed at the second end 34, and a third portion 50 disposed between the first portion 46 and the second portion 48. In the embodiment illustrated in FIG. 5, the inner cavity 42 extends through each of the first, the second, and the third portions 46, 48, 50. However, in other exemplary embodiments, the inner cavity 42 may only extend through the first and third portions 46, 50.

The first portion 46 is configured to be coupled with the shaft 12. More particularly, the distal end 20 of the shaft 12 is open-ended, thereby defining an opening 52 therein. In one exemplary embodiment provided for illustrative purposes only, the inner diameter of the shaft 12, and therefore, the diameter of the opening 52, is approximately 1-2 mm, and the outer diameter of the first portion 46 is slightly smaller. Thus, the first portion 46 is configured to be insertable within the opening 52. Once inserted, the first portion 46 may coupled with and secured to the inner surface of the shaft 12 in a number of ways known in the art. For instance, in one exemplary embodiment, a reflow process may be employed. In another exemplary embodiment, the outer surface of the first portion 46 may be affixed to the inner surface of the shaft 12 using an adhesive, a bonding agent, or any other like material known in the art. Accordingly, those of ordinary skill in the art will appreciate that the shaft 12 and the first portion 46 of the manifold 30 may be coupled together using any number of processes or techniques.

The first portion 46 may be constructed of any number of materials. For example, in an exemplary embodiment the first portion 46 may be constructed of a rigid material, such as a rigid plastic. Alternatively, however, in another exemplary embodiment, the first portion 46 may be constructed of a flexible material such as one or more of the flexible and elastic materials described above. Additionally, as will be described in greater detail below, the first portion 46 may be unitarily-formed with the second and/or third portions 48, 50 of the manifold 30, or may be a separate and distinct component that is ultimately assembled with the second and/or third portions 48, 50 to form the manifold 30.

When inserted within the opening 52 at the distal end 20 of the shaft 12, the inner cavity 42 of the manifold 30 which extends through the first portion 46, is substantially aligned with the irrigation lumen 22. In an exemplary embodiment, the inner diameter of the inner cavity 42 and the outer diameter of the irrigation lumen 22 are such that the tube may be inserted within the inner cavity 42. For instance, in an exemplary embodiment provided for illustrative purposes only, the inner cavity 42 has an inner diameter of approximately 0.8-1.1 mm, and the irrigation lumen 22 has an outer diameter that is slightly smaller. Once inserted, the irrigation lumen 22 may be affixed or otherwise bonded to the inner surface of the inner cavity 42 using techniques known in the art.

With continued reference to FIGS. 4 and 5, the second portion 48 of the manifold 30 is configured to be coupled with the electrode 28. More particularly, the second portion 48 has an outer diameter that is sized so as to be insertable within the cavity or pocket 36 of the electrode 28. In an exemplary embodiment provided for illustrative purposes only, the second portion 48 has an outer diameter of approximately 1-2 mm, and the cavity or pocket 36 has an inner diameter that is slightly larger. Accordingly, the second portion 48 can be inserted within the cavity or pocket 36. Once inserted, the second portion 48 may be coupled with the inner surface of the cavity 36 in a number of ways known in the art. For instance, in one exemplary embodiment, a reflow process may be employed. In another exemplary embodiment, the outer surface of the second portion 48 may be affixed to the inner surface of the cavity 36 using an adhesive, a bonding agent, or any other like material known in the art. Accordingly, those of ordinary skill in the art will appreciate that the electrode 28 and the second portion 48 of the manifold 30 may be coupled together using any number of processes or techniques.

As with the first portion 46, the second portion 48 may be constructed of any number of materials. For example, in an exemplary embodiment, the second portion 48 may be constructed of a rigid material, such as a rigid plastic. Alternatively, however, in another exemplary embodiment, the second portion 48 may be constructed of a flexible material such as one or more of the flexible and elastic materials described above. Further, as with the first portion 46, and as will be described in greater detail below, the second portion 48 may be unitarily-formed with the first and/or third portions 46, 50 of the manifold 30, or may be a separate and distinct component that is ultimately assembled with one or both of the first and third portions 46, 50 to form the manifold 30.

Additionally, in the exemplary embodiment illustrated in FIG. 3, the inner cavity 42 of the manifold 30 extends from the first end 32 of the manifold body 38 through the second end 34, and therefore, through the first, second, and third portions 46, 48, 50. In such an embodiment, the inner cavity 42 is aligned with a fluid passageway 54 disposed within the electrode 28. In this embodiment, the fluid passageway 54 is a through-going passageway in the electrode 28 extending from the cavity or pocket 36 thereof to the outer surface of the electrode 28, and is configured for fluid communication with the inner cavity 42 of the manifold 30. The fluid passageway 54 is similar to the irrigation ports 44 in that it is operative to distribute irrigating fluid flowing through the inner cavity 42 from the electrode 28 and on to the outer surface of electrode 28 and tissue proximate the fluid passageway 54. It should be noted, however, that the present invention is not meant to be limited to an embodiment wherein the electrode 28 includes the fluid passageway 54. Rather, in another exemplary embodiment, the electrode 28 does not include a fluid passageway 54, and the only "irrigation ports" are those in the manifold 30.

With reference to FIGS. 4 and 5, the third portion 50 of the manifold 30 is disposed between the first and second portions 46, 48. The third portion 50 is constructed of one or more flexible materials, and preferably a flexible and elastic material, to allow for the electrode assembly 16, and therefore, the manifold 30 and the electrode 28, to be deflected in one or more directions. More particularly, the third portion 50 is constructed of one or more elastic polymers, such as, for example, silicone, polyurethane, Nylon, PEBAX, and other like materials having similar properties. In an exemplary embodiment, the third portion 50 has an outer diameter that is both greater than the outer diameters of the first and second portions 46, 48, and substantially the same as the outer diameters of one or both of the shaft 12 and the electrode 28. Accordingly, when assembled with the shaft 12 and the electrode 28, the outer surface of the third portion 50 is substantially flush with the outer surfaces of the shaft 12 and the electrode 28.

As illustrated in FIGS. 2-6d, in an exemplary embodiment, the irrigation ports 44 are disposed within the third portion 50. Further, as with the first and second portions 46, 48, and as will be described in greater detail below, the third portion 50 may be unitarily-formed with the first and/or second portions 46, 48 of the manifold 30, or may be a separate and distinct component that is ultimately assembled with one or both of the first and second portions 46, 48 to form manifold 30.

As briefly described above, the manifold 30, and the body 38 thereof, in particular, may be constructed of one or more materials. In one exemplary embodiment, the first, second, and third portions 46, 48, 50 of the manifold 30 are constructed of a single flexible and/or elastic material. In another exemplary embodiment, the first, second, and third portions 46, 48, 50 are constructed of the same material but with the first and second portions 46, 48 being formed of a particular class of the material that has a higher durometer than the particular class of the material of which the third portion 50 is constructed (i.e., the third portion has greater flexibility). In yet another exemplary embodiment, the first and second portions 46, 48 are constructed of an altogether different material than that of the third portion 50. In such an embodiment, the first and second portions 46, 48 may be constructed of a more rigid material than the flexible and/or elastic material of which the third portion 50 is constructed.

Whether the first and second portions 46, 48 are constructed of the same material as the third portion 50, the same type of material but with a higher durometer, or a different material altogether, the manifold 30 may be constructed in a number of ways. In an exemplary embodiment, a molding process, such as a multiple shot molding process, may be used to form the manifold 30 as a single piece wherein the first, second, and third portions 46, 48, 50 of the manifold 30 are unitarily formed. In another exemplary embodiment, one or more of the first, second, and third portions 46, 48, 50 may be separate and distinct components that are assembled with and affixed to the other components. Accordingly, the present invention is not limited to a manifold having one particular construction, but rather manifolds constructed using any number of processes/techniques known in the art remain within the spirit and scope of the present invention.

As briefly described above, and as illustrated in FIGS. 7a and 7b, when the shaft 12, the electrode 28, and the manifold 30 are assembled, the flexible nature of the manifold 30 allows for the electrode assembly 16, and therefore, the manifold 30 and the electrode 28, to be deflected in one or more directions. More particularly, when the electrode 28 contacts tissue and a sufficient amount of force is applied to the electrode 28 against the tissue by the operator of the catheter 10, the manifold 30 is elastically deformed or bent/deflected in a desired direction, thereby deflecting the electrode assembly 16. In an exemplary embodiment, the deflection force applied to the electrode 28 is on the order of 20-50 grams. Once the deflection force is removed, or at least sufficiently reduced, the elastic nature of the manifold material allows for the electrode assembly 16 to bend/deflect back to its original, non-deflected position. It should be noted that the deflection force required is dependent on the particular material used to construct the manifold 30. The higher the durometer or the more stiff the material, the more force will be required, and vice versa. Therefore, the 20-50 gram range for the deflection force is provided for exemplary purposes only.

Figure 7A:
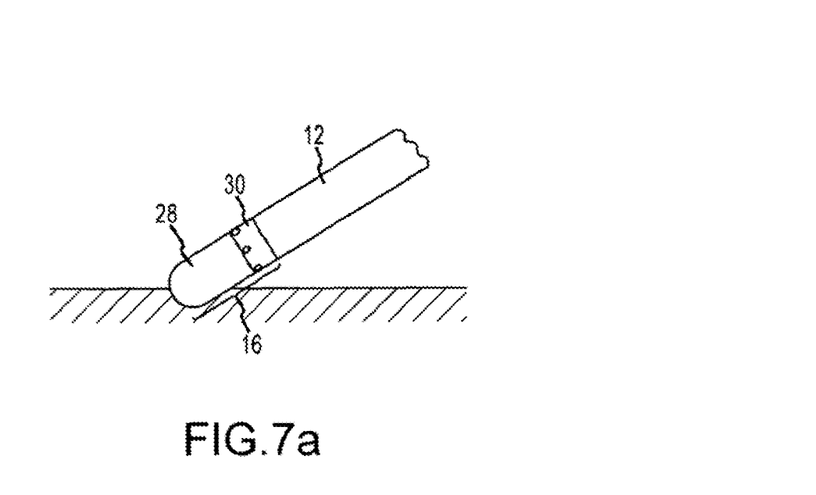
FIG. 7a is a diagrammatic view of the catheter illustrated in FIGS. 1 and 2 contacting tissue, wherein the electrode assembly of the catheter is in a non-deflected position.
Figure 7B:
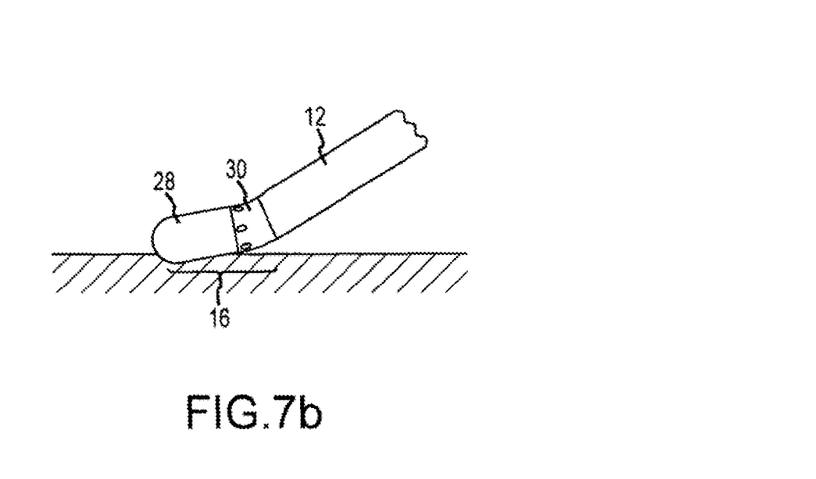
FIG. 7b is a diagrammatic view of the catheter illustrated in FIG. 1 contacting tissue, wherein the electrode assembly of the catheter is in a deflected position.

Accordingly, the flexible manifold 30 allows for increased and improved contact between the electrode 28 and the tissue that is to be ablated. To illustrate this benefit, FIG. 7a depicts the electrode 28 of the catheter 10 in contact with tissue with the electrode assembly 16 in a non-deflected position. Conversely, FIG. 7b illustrates the electrode 28 of the catheter 10 in contact with tissue wherein the electrode assembly 16 is in a deflected position. It is clear from these illustrations that the flexible manifold 30 allows for improved and increased contact between the electrode 28 and the tissue.

Figure 8A:
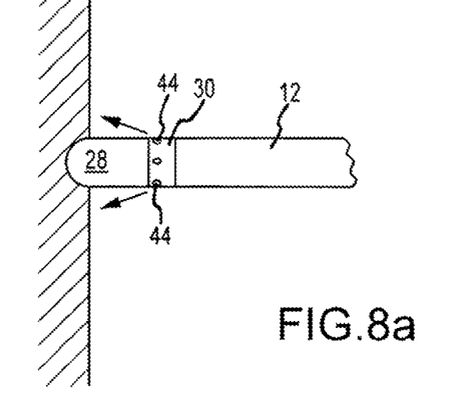
FIG. 8a is a diagrammatic view of the distal portion of the catheter illustrated in FIG. 1 contacting tissue, wherein the electrode assembly of the catheter is in a non-deflected position and the diameters of the irrigation ports are substantially equal to each other.
Figure 8B:
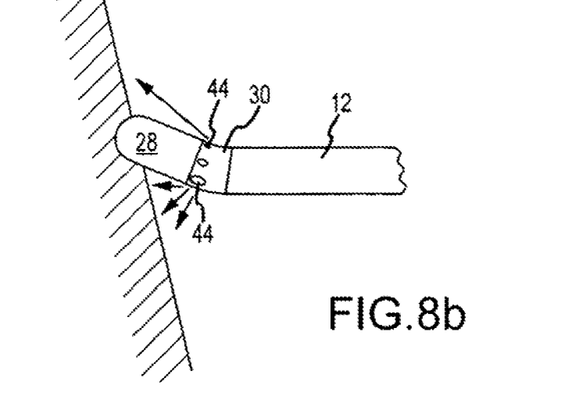
FIG. 8b is a diagrammatic view of the distal portion of the catheter illustrated in FIG. 1 contacting tissue, wherein the electrode assembly of the catheter is in a deflected position and the diameters of the irrigation ports are either expanded or contracted, depending on their location.

With reference to FIGS. 8a and 8b, another aspect of the present invention will be described. As set forth above, in an exemplary embodiment, at least a portion of the manifold 30 is constructed of a flexible and elastic material. In an embodiment wherein the irrigation ports 44 are disposed within this portion of the manifold 30, the elastic nature of the material allows for the irrigating ports 44 to expand and contract (i.e., the diameter of the port gets larger or smaller) as the manifold 30 is elastically deformed or bent/deflected. As a consequence, rather than distributing the irrigating fluid substantially equally through each of the irrigation ports 44, the fluid may be redistributed such that more fluid is distributed through the expanded ports located proximate the ablation site—where it is needed—and less fluid is distributed through the contracted ports located away from the ablation site—where fluid may not be needed. FIGS. 8a and 8b illustrate each of these aspects. As described above, once the deflection force applied to the electrode 28 is removed, or at least sufficiently reduced, the elastic nature of the material allows the electrode assembly 16, and therefore, the manifold 30, to deflect or bend back to its original, non-deflected position, and thus, the irrigation ports 44 likewise return to their original size.

In FIG. 8a, the catheter 10 is in a generally perpendicular relationship with the tissue being ablated and the electrode assembly 16 is in a non-deflected position. In such a relationship, the irrigation ports 44 are generally equal in size to each other and as a result, fluid is substantially equally distributed through each of the irrigation ports 44.

Conversely, in FIG. 8b, the electrode assembly 16 is deflected or bent. As a result, the irrigation ports 44 disposed in the extended area of the manifold 30, or the area of the manifold 30 that is experiencing the most stretch or expansion during the deflection (i.e., on the outside of the "bend" in the manifold 30), expand due to the elasticity of the material. Accordingly, the size of those irrigation ports 44 get larger (i.e., the respective diameters of the ports get larger). On the other hand, the irrigation ports 44 disposed in the area of the manifold 30 that is compressed during the deflection (i.e., on the inside of the "bend" in the manifold 30) contract, thereby reducing the size of those irrigation ports 44 (i.e., the respective diameters of the ports get smaller). The irrigation ports 44 disposed in other areas of the manifold 30 between the most extended area and the most compressed area are incrementally expanded or contracted, respectively, to have a size between the most expanded and most contracted of the irrigation ports 44. The larger the size or diameter of the irrigation port 44, the greater the volume of irrigating fluid that is distributed therefrom.

Figure 9A:
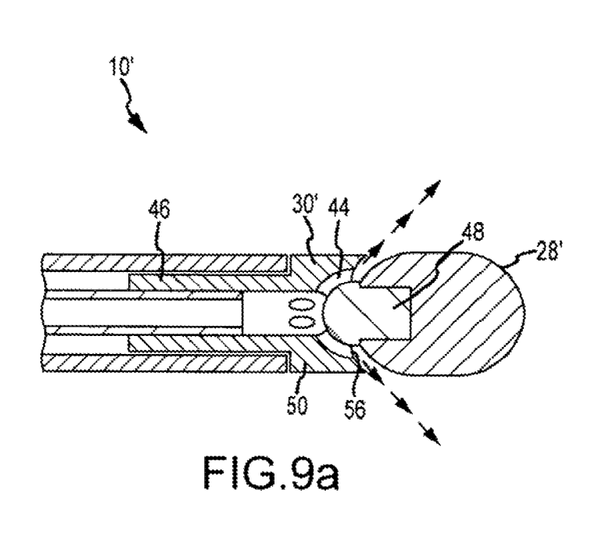
FIG. 9a is a cross-sectional view of the distal portion of another exemplary embodiment of the irrigated ablation catheter illustrated in FIGS. 1-8b, wherein the electrode assembly of the catheter is in a non-deflected position.
Figure 9B:
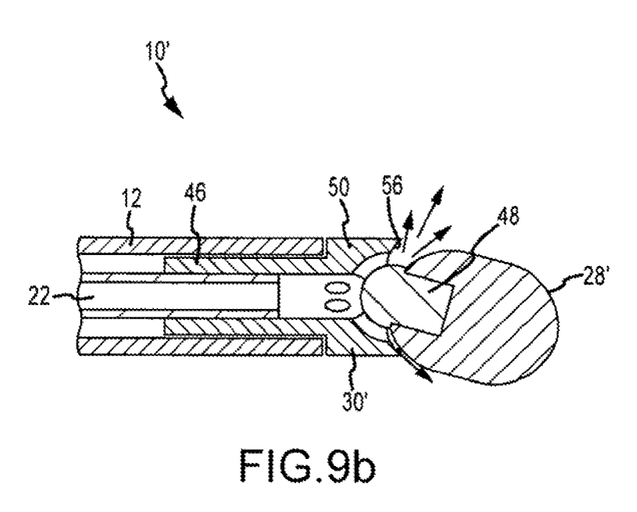
FIG. 9b is a cross-sectional view of the distal portion of the irrigated ablation catheter illustrated in FIGS. 1-8b, wherein the electrode assembly of the catheter is in a deflected position.

FIGS. 9a and 9b illustrate another exemplary embodiment of the catheter 10 (catheter 10') and the electrode assembly 16 (electrode assembly 16'), in particular. Except as provided below, the detailed description set forth above relating to the catheter 10 and the electrode assembly 16 applies here with equal force, and therefore, will not be entirely repeated.

As illustrated in FIG. 9a, the manifold 30 (manifold 30') of electrode assembly 16' is disposed between and coupled to each of the shaft 12 and the electrode 28 (electrode 28'). In an exemplary embodiment, and for reasons that will be discussed in greater detail below, the electrode 28' has a rounded-off proximal end.

With continued reference to FIG. 9a, in an exemplary embodiment, the first portion 46 of the manifold 30' is configured to be coupled with the shaft 12, the second portion 48 is configured to be coupled with the recess or pocket 36 in the electrode 28', and the third portion 50 is disposed between the first and second portions 46, 48. As with the embodiment described above, the irrigation ports 44 are disposed within the third portion 50. In this embodiment, the third portion 50 includes a concave surface 56 disposed in the distal end thereof (i.e., in the end of the third portion 50 facing the electrode 28'). Additionally, the irrigation ports 44 are disposed within the concave surface such that the exterior openings of the irrigation ports 44 substantially face the electrode 28'. Further, for reasons that will be discussed in greater detail below, the concave surface 56 has a concave shape that it is complementary to the rounded-off shape of the proximal end of the electrode 28'.

With reference to FIG. 9b, and as with the embodiment of the manifold 30 described above, at least a portion of the manifold 30' is constructed of one or more flexible and/or elastic materials. Suitable materials include, without limitation, silicone, polyurethane, Nylon, and PEBAX. In an exemplary embodiment, it is the second portion 48 that is constructed of a flexible material. However, it should be noted that in addition to second portion 48, the first and third portions 46, 50 may also, or alternatively, be constructed of a flexible material. As described above, the first and the third portions may also be constructed of a more rigid plastic material, for example.

As illustrated in FIG. 9b, the second portion 48 is constructed of flexible material to allow for the electrode assembly 16', and therefore, the manifold 18' and the electrode 28', to be deflected. As described in greater detail above, when the electrode 28' contacts tissue and a deflection force is applied to the electrode 28' against the tissue by the operator of the catheter 10', the manifold 30', and in this embodiment, the second portion 48 thereof, in particular, is elastically deformed or bent/deflected. As a result, the electrode assembly 16' and the electrode 28' coupled to the second portion 46 is caused to be deflected. As the electrode assembly 16' is deflected, the rounded-off proximal end of electrode 28' makes contact with the complementary-shaped concave surface 56 of the third portion 50 of the manifold 30'. Since the irrigation ports 44 are located in the concave surface 56, as the electrode assembly 16' is further deflected, the electrode 28' begins to close off the irrigation ports 44 disposed in the deflection path (i.e., on the "inside" of the bend or deflection), thereby blocking the flow of irrigating fluid from those ports. Once the electrode assembly 16' is fully deflected, the electrode 28' substantially limits the distribution of irrigating fluid from the irrigation ports 44 disposed in the deflection path.

Conversely, as the electrode assembly 16' deflects, the electrode 28' also opens or increases the flow path from the irrigation ports 44 disposed opposite the deflection path (i.e., on the "outside" of the bend or deflection) proximate the ablation site. Consequently, the distribution of irrigating fluid from these irrigation ports is increased. Accordingly, the irrigating fluid is redistributed such that more irrigating fluid is distributed through the irrigation ports 44 proximate the ablation site—where more fluid is needed—and less irrigating fluid is distributed from the irrigation ports 44 that are disposed away from the electrodes that are ablating tissue—where little or no irrigating fluid is needed. Therefore, in this embodiment, the electrode assembly 16', and the electrode 28', in particular, acts to "open" and "close" the irrigation ports 44, or increase and decrease the flow paths from the irrigation ports as the electrode assembly 16' is deflected.

Figure 10:
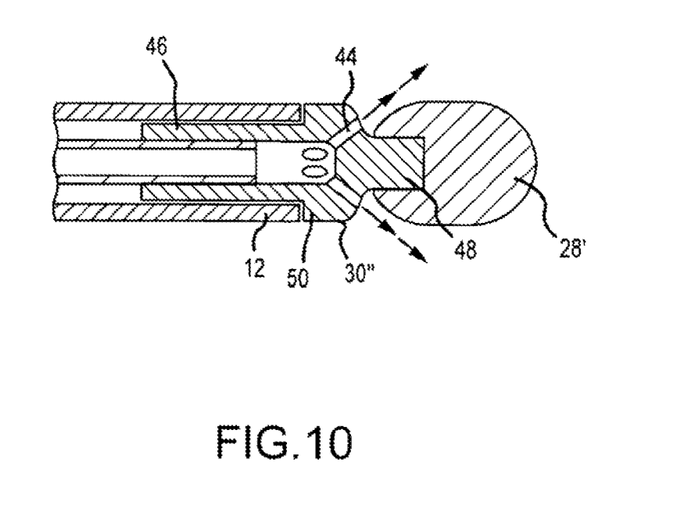
FIG. 10 is a cross-sectional view of the distal portion of another embodiment of the irrigated ablation catheter illustrated in FIGS. 9a and 9b, wherein the electrode assembly is in a non-deflected position.

It should be noted that the embodiment illustrated in FIGS. 9a and 9b having a concave surface as the distal end of the manifold 30' is provided for exemplary purposes only and is not meant to be limiting in nature. Rather, those of ordinary skill in the art will appreciate that the manifold 30 may take on a number of constructions or arrangements that remain within the spirit and scope of the present invention. For example, FIG. 10 illustrates another exemplary embodiment wherein the distal end of the third portion 50 of the manifold 30 (30") has a tapered or conical shape.

In this embodiment, the irrigation ports 44 are disposed in the surface of the third portion proximate the electrode 28'. When the electrode assembly 16' is in a substantially non-deflected position, all of the irrigation ports 44 are open, and thus, the distribution of irrigating fluid from each of the irrigation ports 44 is substantially equal. As the electrode assembly 16' is deflected, the irrigation port(s) 44 in the path of the deflection (i.e., on the "inside of the bend/deflection) is/are closed off, thereby blocking or impeding the flow of irrigating fluid from those irrigation ports. The irrigating ports 44 that are not in the deflection path remain open, and therefore, the irrigating fluid is redistributed such that more irrigating fluid is distributed through the irrigation ports 44 proximate the ablation site, and less irrigating fluid is distributed from the irrigation ports 44 that are disposed away from the ablation site.

Figure 11:
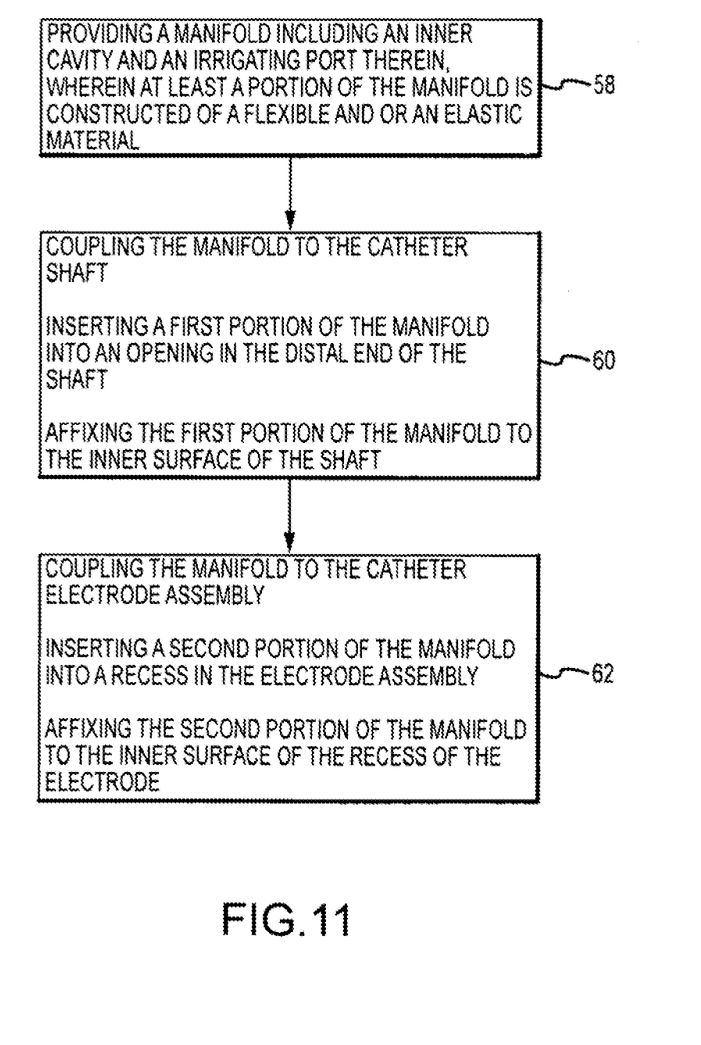
FIG. 11 is a flow chart illustrating a method of manufacturing an irrigated ablation catheter in accordance with the present teachings.

With reference to FIG. 11, a method of manufacturing an irrigating ablation catheter comprising a shaft 12 and an electrode 28 will be described. In a first step 58, a manifold 30 having at least a portion constructed of a flexible material is provided. The manifold 30 further includes an inner cavity 42 and plurality of irrigation ports 44 disposed therein. In another exemplary embodiment, the providing step 58 includes providing a manifold 30 that is constructed of a flexible and elastic material.

In a second step 60, a first end 32 of the manifold 30 is coupled with the distal end 20 of the shaft 12. In an exemplary embodiment, the second step 60 comprises inserting a first portion 46 of the manifold 30 into an opening 52 in the distal end 20 of the shaft 12, and affixing the first portion 46 to the shaft 12. Numerous techniques or processes may be used to affix the components together. In one exemplary embodiment, a reflow process may be employed. In another exemplary embodiment, the outer surface of the first portion 46 may be affixed to the inner surface of the shaft 12 using an adhesive, a bonding agent, or any other like material known in the art. Accordingly, those of ordinary skill in the art will appreciate that the shaft 12 and the first portion 46 of the manifold 30 may be coupled together using any number of processes or techniques.

In a third step 62, the second end 34 of the manifold 30 is coupled with the proximal end of the electrode 28. In an exemplary embodiment, the third step 62 comprises inserting a second portion 48 of the manifold 30 into a recess or pocket 36 in the proximal end of the electrode 28, and affixing the second portion 48 to the electrode 28, and the inner surface of the recess/pocket 36, in particular. Numerous techniques or processes may be used to affix the components together. In one exemplary embodiment, a reflow process may be employed. In another exemplary embodiment, the outer surface of the second portion 48 may be affixed to the inner surface of the electrode 28, and more particularly, the inner surface of the recess or pocket 36, using an adhesive, a bonding agent, or any other like material known in the art. Accordingly, those of ordinary skill in the art will appreciate that the electrode 28 and the second portion 48 of the manifold 30 may be coupled together using any number of techniques.

Although only certain embodiments of this invention have been described above with a certain degree of particularity, those skilled in the art could make numerous alterations to the disclosed embodiments without departing from the scope of this invention. For example, the manifold may be constructed of any number of flexible and elastic materials. Further, the shaft, manifold, and electrode assembly of the catheter may be assembled in any number of ways. Still further, the manifold component may be assembled or formed in various ways. Additionally, all directional references (e.g., up, down, left, right) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. It is intended that all matter contained in the above description or shown in the accompanying drawings shall be interpreted as illustrative only and not limiting. Changes in detail or structure may be made without departing from the invention as defined in the appended claims.

What is claimed is:

1. A catheter comprising:
   a shaft with a proximal end and a distal end;
   an electrode assembly connected to the distal end of the shaft, the electrode assembly configured to deflect under an application of a deflection force to the electrode assembly, wherein the shaft has a sufficient rigidity and flexibility for supporting an amount of force applied by an operator of the catheter to cause a bending of the electrode assembly; and
   an irrigation lumen passing through the shaft and in fluid communication with the electrode assembly, wherein upon application of force to the electrode assembly from a first direction the electrode assembly is configured to distribute irrigation fluid in at least the first direction, from a first side of the electrode assembly, and to reduce a distribution of irrigation fluid in at least a second direction, from a second side of the electrode assembly wherein the second side of the electrode assembly is disposed opposite of the first side of the electrode assembly further wherein the electrode assembly is configured to distribute irrigation fluid in at least the second direction, from the second side of the electrode assembly, and to reduce the distribution of irrigation fluid in at least the first direction, from the first side of the electrode upon application of force to the electrode assembly from the second direction, wherein the electrode assembly is configured to distribute irrigation fluid in the first direction by expanding from the first side upon application of force to the electrode assembly from the first direction, and wherein the electrode assembly is configured to distribute irrigation fluid in the second direction by expanding from the second side upon application of force to the electrode assembly from the second direction.

2. The catheter of claim 1, wherein the second side of the electrode assembly disposed opposite the deflection force is configured to contract upon application of force to the electrode assembly from the first direction.

3. The catheter of claim 1, wherein a portion of the electrode assembly is configured to directionally proportion fluid.

4. The catheter of claim 3, wherein the portion of the electrode assembly configured to distribute irrigation fluid is formed from an elastic material.

5. The catheter of claim 1, wherein the portion of the electrode assembly has a flexibility greater than a flexibility of a portion of the shaft located adjacent to the electrode assembly.

6. The catheter of claim 1, wherein:
the second side of the electrode assembly is disposed radially opposite of the first side of the electrode assembly; and
the distribution of irrigation fluid in the at least first direction is in a radially opposite direction with respect to distribution of irrigation fluid in the at least second direction.

7. An irrigated ablation catheter, comprising:
a shaft comprising a proximal end, a distal end, and an irrigation lumen;
an ablation electrode; and
a manifold disposed between and coupled to the distal end of the shaft and the ablation electrode and in fluid communication with the irrigation lumen, wherein the manifold has a flexibility greater than a flexibility of a portion of the shaft located immediately adjacent to the ablation electrode and is configured to directionally proportion irrigation fluid based on deflection of a tip of the ablation electrode, wherein the manifold further comprises a plurality of irrigation ports extending between an inner surface and an outer surface of the manifold and in fluid communication with the irrigation lumen to distribute irrigation fluid through the plurality of irrigation ports, wherein deflection of the manifold causes irrigation fluid from the irrigation lumen to be redistributed through the plurality of irrigation ports disposed along a first side of the manifold, wherein the first side of the manifold is configured to be located proximate to an ablation site; wherein a size of the irrigation ports disposed along the first side of the manifold is expanded and a size of the irrigation ports disposed along a second side of the manifold is contracted in response to the deflection of the manifold, and wherein more fluid from the irrigation lumen is redistributed through the expanded irrigation ports configured to be located proximate to the ablation site than the contracted irrigation ports configured to be located away from the ablation site in response to the deflection of the tip of the ablation electrode.

8. The irrigated ablation catheter of claim 7, wherein the manifold is formed from a flexible material.

9. The irrigated ablation catheter of claim 8, wherein the flexible material has a flexibility greater than that of the shaft.

10. The irrigated ablation catheter of claim 7, wherein the manifold is formed from an elastic material.

11. The irrigated ablation catheter of claim 7, wherein the manifold is formed from an electrically nonconductive material.

12. The irrigated ablation catheter of claim 7, wherein the plurality of irrigation ports are radially dispersed around a circumference of the manifold.

13. An irrigated ablation catheter, comprising:
a shaft comprising a proximal end, a distal end, and an irrigation lumen disposed therein;
an electrode assembly comprising a manifold, wherein the manifold has a flexibility greater than a flexibility of a portion of the shaft disposed adjacent to the electrode assembly, wherein:
the manifold is coupled to the distal end of the shaft and includes a body defined by an outer surface and an inner surface, an inner cavity disposed within the body configured for fluid communication with the irrigation lumen, wherein the outer surface is in fluid communication with the inner surface;
an ablation electrode is coupled to a distal end of the manifold, wherein deflection of the manifold and the ablation electrode cause fluid to be distributed from the inner cavity to a portion of the outer surface of the manifold disposed opposite a deflection path of the electrode assembly and reduces a fluid flow from the inner cavity to a portion of the outer surface of the manifold disposed along the deflection path of the electrode assembly, wherein the portion of the outer surface disposed opposite the deflection path is located radially opposite of the portion of the outer surface disposed along the deflection path; and
the electrode assembly is configured to distribute irrigation fluid in a first direction by expanding from a first side upon application of force to the electrode assembly from the first direction, and wherein the electrode assembly is configured to distribute irrigation fluid in a second direction by expanding from a second side upon application of force to the electrode assembly from the second direction, wherein the first side is located radially opposite of the second side.

14. The irrigated ablation catheter of claim 13, wherein:
the portion of the outer surface disposed opposite the deflection path of the electrode assembly includes an irrigation port disposed in the deflection path; and
a size of the irrigation port disposed opposite the deflection path of the electrode assembly is expanded upon deflection of the manifold.

15. The irrigated ablation catheter of claim 14, wherein the size of the irrigation port disposed in the deflection path of the electrode assembly is contracted upon deflection of the manifold.

16. The irrigated ablation catheter of claim 14, wherein a flow of irrigation fluid through the irrigation port disposed in the deflection path of the electrode assembly is reduced.

\* \* \* \* \*